United States Patent
Himmeldirk et al.

(10) Patent No.: US 7,772,381 B2
(45) Date of Patent: Aug. 10, 2010

(54) EFFICIENT METHOD TO SYNTHESIZE BENZYL GROUP-PROTECTED ALPHA-PENTAGALLOYLGLUCOSE (α-PGG) AND ITS ANALOGUES

(75) Inventors: Klaus B. Himmeldirk, Vincent, OH (US); Xiaozhou Chen, Athens, OH (US)

(73) Assignee: Ohio University, Athens, OH (US)

( * ) Notice: Subject to any disclaimer, the term of this patent is extended or adjusted under 35 U.S.C. 154(b) by 284 days.

(21) Appl. No.: 10/597,398

(22) PCT Filed: Jan. 24, 2005

(86) PCT No.: PCT/US2005/002261

§ 371 (c)(1),
(2), (4) Date: Sep. 8, 2008

(87) PCT Pub. No.: WO2005/072765

PCT Pub. Date: Aug. 11, 2005

(65) Prior Publication Data

US 2008/0319185 A1    Dec. 25, 2008

Related U.S. Application Data

(60) Provisional application No. 60/539,063, filed on Jan. 23, 2004.

(51) Int. Cl.
*C07H 15/00*    (2006.01)
*C07H 17/00*    (2006.01)
*C07G 3/00*    (2006.01)

(52) U.S. Cl. .................... 536/18.6; 536/18.5

(58) Field of Classification Search ............... None
See application file for complete search history.

(56) References Cited

OTHER PUBLICATIONS

Khanbabaee et al. Tetrahedron (1997), vol. 53, pp. 10725-10732.*

\* cited by examiner

*Primary Examiner*—Patrick T Lewis
(74) *Attorney, Agent, or Firm*—Calfee, Halter and Griswold LLP

(57) ABSTRACT

A method to synthesize benzyl group protected alpha-pentagalloylglucose (α-PGG) and related compounds. The method comprises the steps of: suspending a highly reactive acylation agent and an acylating catalyst in a donor solvent; adding α-D-glucose or an analogue thereof to the mixture; reacting the mixture at room temperature for a time sufficient for reaction to occur; evaporating the solvent; taking up the residue in an appropriate solvent; filtering the residue and solvent mixture; and evaporating off the solvent.

27 Claims, 2 Drawing Sheets

EFFICIENT METHOD TO SYNTHESIZE BENZYL GROUP-PROTECTED ALPHA-PENTAGALLOYLGLUCOSE (α-PGG) AND ITS ANALOGUES

CROSS-REFERENCE TO RELATED APPLICATION

This application claims priority to U.S. Provisional Application No. 60/539,063 filed Jan. 23, 2004, the entirety of which is incorporated herein by reference.

BACKGROUND OF THE INVENTION

α-PGG has been shown to possess anti-diabetic and other bioactivities that make it a target for the development of new drugs. Since is does not occur in nature, it must be prepared by a multi-step synthesis. Currently known procedures to synthesize α-PGG comprise two main steps: an initial acylation reaction generates benzyl group-protected α-PGG. This precursor must be isolated in order to obtain pure α-PGG in the final hydrogenation reaction. The first step (acylation) produces large amounts of side products that are very difficult to remove. The most important of these unwanted chemicals are the β-isomer of the PGG precursor, dialkyl urea, and N-acylurea derivatives. Chromatography, which is quite expensive, is the only technique that allows for the purification of benzyl-group protected α-PGG. Only gram quantities of the target compound can be produced. The high costs of chromatography and the difficulties in scale-up procedures suitable for producing kilogram to ton quantities of product preclude industrial application of the procedure.

Accordingly, a need exists for better methods of producing the precursors of α-PGG. The new methods should eliminate the need for chromatography, and should be amenable to scaling up to kilogram or ton quantities.

SUMMARY OF THE INVENTION

Provided is a new method to synthesize a key precursor of alpha-pentagalloylglucose (α-PGG). The new process reduces the costs for synthesis of α-PGG by more than 60%. The method allows for the production of the precursor on a kilogram to ton scale. Moreover, it can be used to efficiently synthesize analogues of α-PGG that are modified in the carbohydrate or acyl parts of the molecule.

The method described herein comprises the steps of: (a) suspending a highly reactive acylation agent and an acylating catalyst in a donor solvent; (b) adding α-D-glucose or an analogue thereof to the mixture; (c) reacting the mixture at room temperature for a time sufficient for reaction to occur; (d) evaporating the solvent; (e) taking up the residue in an appropriate solvent; (f) filtering the residue and solvent mixture; and (g) evaporating off the solvent.

In some embodiments, the highly reactive acylation agents are acid chlorides. A suitable class of acylating catalysts are pyridine derivatives, though other acylating catalysts may be determined by those skilled in the art. In some embodiments, the acylating catalyst is 4-(N,N-dimethylamino)pyridine (DMAP). Some suitable α-D-glucose analogues are those in which the analogue is selected from hexoses, pentoses, and tetroses, or wherein the ring oxygen is replaced by a carbon, nitrogen or sulfur In some embodiments, the solvents chosen produce an α:β ratio of at least 90:10; in other embodiments, the solvents chosen produce an α:β ratio of at least 95:5. In some embodiments described herein, the solvents include acetonitrile, 1,4-dioxane and THF. In many embodiments, the solvent is acetonitrile.

After the addition of the acylating catalyst, the mixture is stirred at room temperature until the acylation agent is dissolved. In some embodiments, this tales about 5 to 10 minutes.

The mixture is generally allowed to react at room temperature for a sufficient time, which may be determined by those skilled in the art. In some embodiments, the mixture is allowed to react for several hours. In some embodiments, the mixture is allowed to react at room temperature until the solvent has evaporated off. In some embodiments, the solvent used for taking up the residue in step (e) is toluene, heated to about 60° C. When a heated solvent is used, the solvent and residue mixture are allowed to cool to room temperature prior to the filtration step.

DETAILED DESCRIPTION OF THE INVENTION

Known methods for synthesizing the α-PGG precursor rely on a procedure that uses a carbodiimide coupling agent, such as DCC, in conjunction with N,N-dimethylaminopyridine (DMAP) as a catalyst. See, e.g., *Tetrahedron*, Vol. 53, No. 31, pp. 10725-10732 (1997). This procedure is suitable only for small-scale synthesis of the α-PGG precursor because of the large number of side products produced. Additionally, a time consuming and expensive chromatographic purification step is necessary. In addition, the carbodiimide reagents used in the process are strong sensitizers, which would pose a severe health risk for the operators of large-scale production facilities.

Provided herein are new methods of producing the key precursor of α-PGG using different reagents than conventional methods. The reagents used in the new methods are used in smaller quantities than the amounts of reagents used in previous methods. The new methods also eliminate the need for chromatography to remove side products. In addition, the new methods can be run at room temperature, avoiding costs incurred by heating and/or cooling the reaction mixture. Overall, the new process is highly cost efficient, and it allows for synthesis of ton quantities of the α-PGG precursor. Moreover, it allows for synthesis of analogues of benzyl-group protected α-PGG that are modified in the carbohydrate or acyl parts of the molecule.

Figure 1:
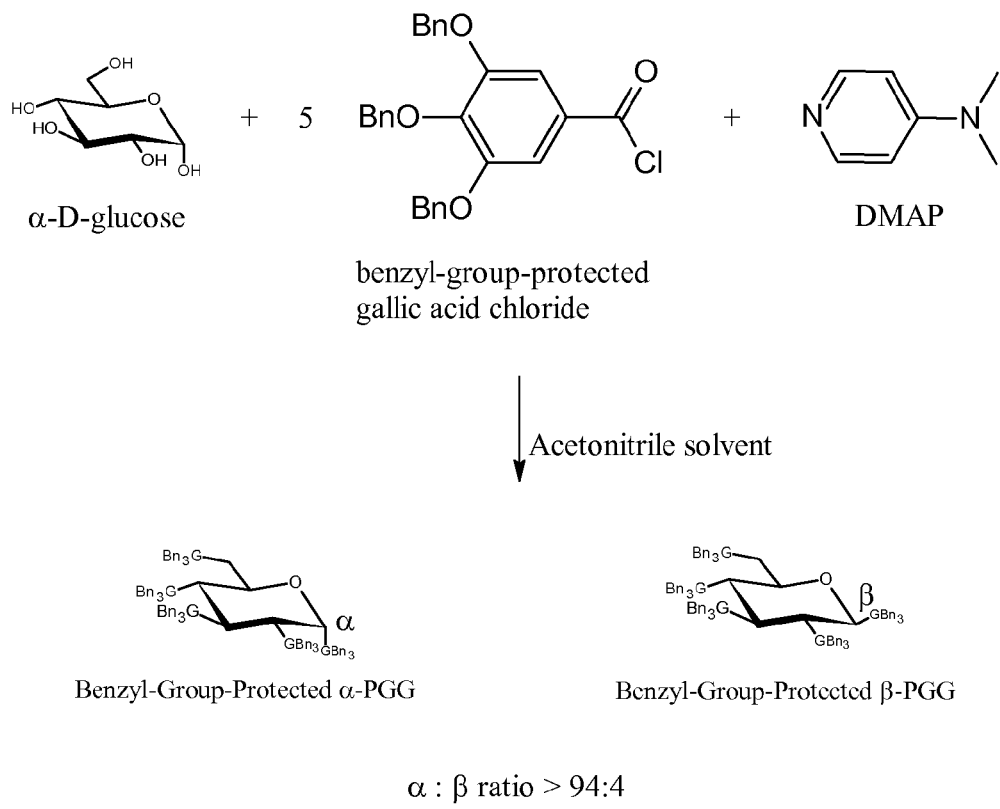
FIG. 1 illustrated the synthetic scheme described herein.
Figure 2:
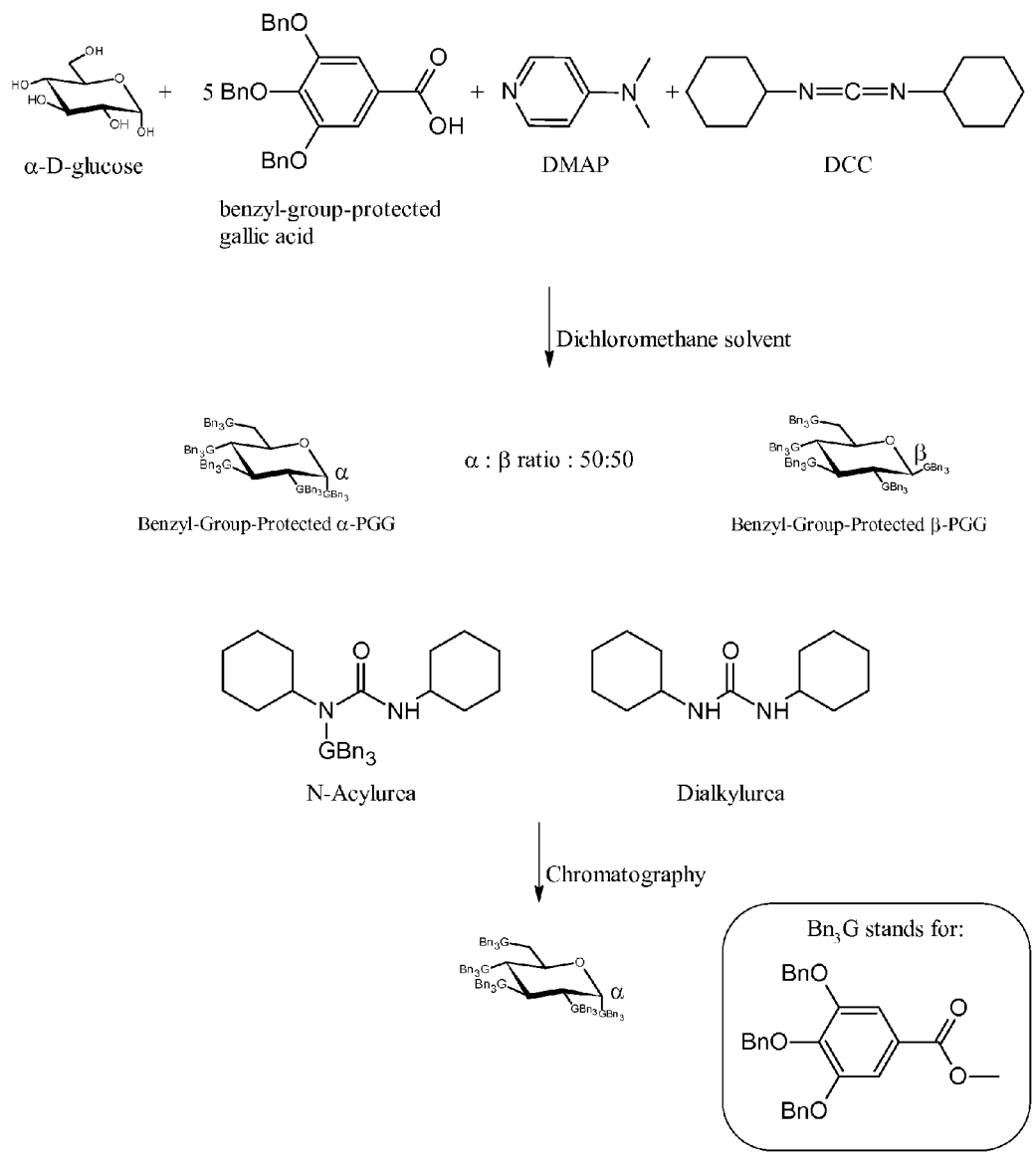
FIG. 2 illustrates the state of the art process for synthesizing benzyl group protected α-PGG.

FIG. 1 shows the synthetic scheme described herein. Using the method described herein, the no chromatography step is necessary, which greatly reduces production cost and allows large scale production of α-PGG or analogues thereof. The small amounts of β-isomer that are formed may easily be removed after the final steps in the PGG synthesis, removal of the benzyl groups by hydrogenation. The yield of the method is almost quantitative. FIG. 2 shows the state of the art synthetic scheme for the production of benzyl group protected α-PGG. The final chromatographic step is very expensive and precludes production on an industrial scale. A complete separation of the α- and β-isomers of the benzyl group-protected PGG is extremely difficult.

For the first step of production of α-PGG and its analogues (acylation) highly reactive acylation agents, such as acid chlorides, are used. In addition, the solvent used for the reaction is chosen to favor formation of the α-isomer and suppress formation of the β-isomer of the PGG, or PGG analogue, precursor. In some embodiments, the solvent chosen yields an α:β ratio of greater than 90:10. In other embodiments, the solvent chosen yields an α:β ratio of greater than 95:5. Suitable solvents include donor solvents such as, but not limited to, acetonitrile, 1,4-dioxane, and tetrahydrofuran. Acetonitrile is used as the solvent in many embodiments described herein. Moreover, the methods of described herein produce no dialkylurea or N-acylurea side products during the reaction process. Additionally, the yields of the reaction is almost quantitative, greater than 95%.

The coupling of the benzyl-group protected gallic acid with the α-D-glucose starting material to obtain the precursor of α-PGG and its analogs is performed using a highly reactive acylating agent, such as an acid chloride. This ensures that α-D-glucose reacts with the acylating agent before it can rearrange to β-D-glucose. This, in turn, avoids the formation of the β-isomer of the PGG precursor, or PGG analogue precursor. The choice of a solvent, such as acetonitrile, that yields a high α:β ratio is a second factor that helps to achieve a very high α:β ratio in the products.

Additionally, the use of an acid chloride in the reaction, makes it unnecessary to use a carbodiimide coupling agent. This, in turn, avoids the formation of the dialkylurea and N-acylurea side products. This eliminates the need for chromatographic purification.

Also provided herein are methods of making precursors of α-PGG analogues. The methods described herein are useful for making analogues of α-PGG in which the glucose part of the PGG is substituted by other sugars, such as hexoses, pentoses, or tetroses. The hexoses used in some embodiments include galactose, mannose, idose, talose, altrose, allose, gulose, fructose, or similar. The pentoses used in some embodiments include xylose, ribose, arabinose, and lyxose. The tetroses used in some embodiments include threose and erythrose. Those skilled in the art would also recognize other hexoses, pentoses, and tetroses that may be used. The methods described herein are also useful for making analogs in which the glucose part of the PGG is substituted by sugar analogues, of glucose, other hexoses, pentoses, or tetroses, in which the ring oxygen of the sugar analogue is substituted by carbon, nitrogen, or sulfur. The methods described herein are also useful for making analoguages wherein the gallic acid part of the PGG is replaced by other phenols. In some embodiments, the phenols are chosen from 2,3-dihydroxybenzoic acid, 3,4-dihydroxybenzoic acid, and 3,5-dihydroxybenzoic acid. Other phenols may also be used. Those skilled in the art would be able to recognize other modifications of the α-PGG precursor that could be prepared by the methods described herein.

Materials and Methods

The names and Chemical Abstracts register numbers of the benzyl group-protected PGG's are: α-D-glucopyranose pentakis[3,4,5-tris(phenylmethoxy)benzoate] (CA Reg. No. 70424-95-2) and β-D-glucopyranose pentakis[3,4,5-tris (phenylmethoxy)benzoate] (CA Reg. No. 122625-60-9).

The acid chloride (459 mg, 1.0 mmol) and DMAP (128 mg, 1.05 mmol) were suspended in 10 mL acetonitrile at room temperature. After stirring for 5 to 10 minutes, a clear solution formed. Finely powdered α-D-glucose (36.0 mg, 0.2 mmol) was added. The mixture was stirred at room temperature for 18 hours. The residue was taken up in 5 mL of toluene at 60° C. After cooling to room temperature, the solution was filtered through a layer of silica gel (250 mg, 1.2 cm thick). The silica gel was washed with 5 mL of a mix of toluene and ethyl acetate (100:4) to elute any product that may have stuck to the silica gel. The solvent was evaporated. The product was obtained as highly viscous oil after drying it in an oil pump vacuum for 5 hours. The yield was 455 mg (99%).

The examples described herein are illustrative of the methods described herein and not meant to limit scope of the invention.

The invention claimed is:

1. A method for the synthesis of a benzyl group-protected alpha-galloylmonosaccharide consisting essentially of the steps of:
   a) suspending a highly reactive acylation agent and an acylating catalyst in a donor solvent;
   b) adding a monosaccharide to the mixture; and
   c) reacting the mixture at room temperature for a time sufficient for reaction to occur;
   wherein the reaction product comprises the benzyl group-protected alpha-galloylmonosaccharide.

2. The method of claim 1 further consisting essentially of the steps of:
   d) evaporating the solvent from the mixture of step (c);
   e) taking up the residue in an second solvent;
   f) filtering the residue and second solvent mixture; and
   g) evaporating off the second solvent.

3. The method of claim 2 further consisting essentially of the step of hydrogenating the product of step (g) to yield an alpha-galloylmonosaccharide.

4. The method of claim 1 wherein the highly reactive acylating agent is an acid chloride.

5. The method of claim 1 wherein the acylating catalyst is a pyridine derivative.

6. The method of claim 5 wherein the pyridine derivative is 4-(N,N-dimethylamino)pyridine (DMAP).

7. The method of claim 1 wherein the monosaccharide is selected from the group consisting of hexoses, pentoses, and tetroses.

8. The method of claim 7 wherein the ring oxygen of the hexoses, pentoses, and tetroses has been replaced with an atom selected from the group consisting of carbon, nitrogen, and sulfur.

9. The method of claim 7 wherein the monosaccharide is a hexose.

10. The method of claim 9 wherein the hexose is selected from the group consisting of glucose, galactose, mannose, idose, talose, altrose, allose, gulose, fructose, and combinations thereof.

11. The method of claim 7 wherein the monosaccharide is a pentose.

12. The method of claim 11 wherein the pentose is selected from the group consisting of xylose, ribose, arabinose, lyxose, and combinations thereof.

13. The method of claim 7 wherein the monosaccharide is a tetrose.

14. The method of claim 13 wherein the tetrose is selected from the group consisting of threose, erythrose, and combinations thereof.

15. The method of claim 1 wherein the mixture of step (c) is allowed to react for several hours.

16. The method of claim 1 wherein the donor solvent is selected to produce a ratio α-galloylmonosaccharide to β-galloylmonosaccharide (α:β ratio) of at least 90:10.

17. The method of claim 16 wherein the donor solvent is selected to produce an α:β ratio of at least 95:5.

18. The method of claim 1 wherein the donor solvent is selected from the group consisting of acetonitrile, 1,4-dioxane, and tetrahydrofuran.

19. The method of claim 18 wherein the donor solvent is acetonitrile.

20. The method of claim 2 wherein the second solvent is toluene.

21. The method of claim 2 wherein the second solvent is heated.

22. The method of claim 1 wherein the α:β ratio is greater than 90:10.

23. The method of claim 22 wherein the α:β ratio is greater than 95:5.

24. The method of claim 10 wherein the hexose is glucose.

25. The method of claim 24 wherein the glucose is D-glucose.

26. The method of claim 25 wherein the D-glucose is α-D-glucose.

27. The method of claim 1 wherein the monosaccharide is an α-monosaccharide.

* * * * *